(12) United States Patent
Hengerer (10) Patent No.: US 12,268,561 B2
(45) Date of Patent: Apr. 8, 2025

(54) APPARATUS AND METHOD FOR ORIENTING AN INSTRUMENT RELATIVE TO A TARGET OBJECT

(71) Applicant: Siemens Healthcare GmbH, Erlangen (DE)

(72) Inventor: Arne Hengerer, Möhrendorf (DE)

(73) Assignee: Siemens Healthineers AG, Forchheim (DE)

( * ) Notice: Subject to any disclaimer, the term of this patent is extended or adjusted under 35 U.S.C. 154(b) by 389 days.

(21) Appl. No.: 17/126,654

(22) Filed: Dec. 18, 2020

(65) Prior Publication Data
US 2021/0212791 A1    Jul. 15, 2021

(30) Foreign Application Priority Data
Jan. 10, 2020    (DE) .................. 102020200239.8

(51) Int. Cl.
| | |
|---|---|
| *A61B 90/11* | (2016.01) |
| *A41D 13/12* | (2006.01) |
| *A61B 17/17* | (2006.01) |
| *A61B 18/00* | (2006.01) |
| *A61B 18/14* | (2006.01) |
| *A61B 34/10* | (2016.01) |

(52) U.S. Cl.
CPC .......... *A61B 90/11* (2016.02); *A41D 13/1236* (2013.01); *A61B 17/1739* (2013.01); *A61B 18/14* (2013.01); *A61B 2018/00577* (2013.01); *A61B 2034/105* (2016.02)

(58) Field of Classification Search
CPC ...... A61B 90/11; A61B 17/1739; A61B 18/14
See application file for complete search history.

(56) References Cited

U.S. PATENT DOCUMENTS

| | | | |
|---|---|---|---|
| 5,375,588 A | 12/1994 | Yoon | |
| 5,702,406 A | 12/1997 | Vilsmeier | |
| 8,800,569 B2 * | 8/2014 | Whitmore, III | ...... A61F 5/3769 128/845 |

(Continued)

FOREIGN PATENT DOCUMENTS

| | | |
|---|---|---|
| DE | 4432891 A1 | 3/1996 |
| WO | 2012175477 A1 | 12/2012 |

OTHER PUBLICATIONS

NBK LLC ((May 27, 2014). Secure workpiece easily and reliably introducing "clamping screws with eccentric head": NBK: The Motion Control Components. NBK. Retrieved Feb. 17, 2023, from https://www.nbk1560.com/en/resources/specialscrew/article/locatingscrewpoint/?SelectedLanguage=en). (Year: 2014).*

(Continued)

*Primary Examiner* — Jennifer Pitrak McDonald
*Assistant Examiner* — Megan T Fedorky
(74) *Attorney, Agent, or Firm* — Lempia Summerfield Katz LLC (57) ABSTRACT

The disclosure relates to an apparatus and to a method for fixing a target object in place and for orienting an instrument relative to the target object which has been fixed in place. The target object is here fixed in place by a first mask element. A second mask element is arranged on the outside thereof. By an adjusting facility, the second mask element may then be shifted relative to the first mask element, whereby the instrument retained by or passed through the second mask element is oriented.

15 Claims, 2 Drawing Sheets

(56) References Cited

U.S. PATENT DOCUMENTS

| | | |
|---|---|---|
| 9,950,191 B2* | 4/2018 | Nieberding .......... A61B 6/0428 |
| 2010/0160771 A1 | 6/2010 | Gielen |
| 2014/0206924 A1 | 7/2014 | Nieberding |
| 2015/0053213 A1* | 2/2015 | Nieberding .............. A61N 5/10 |
| | | 128/869 |

OTHER PUBLICATIONS

Printout taken Aug. 12, 2023: ((May 27, 2014). Secure workpiece easily and reliably introducing "clamping screws with eccentric head": NBK: The Motion Control Components. NBK. Retrieved Aug. 12, 2023, from https://www.nbk1560.com/en/resources/specialscrew/article/locatingscrewpoint/?SelectedLanguage=en (Year: 2014).*

* cited by examiner

APPARATUS AND METHOD FOR ORIENTING AN INSTRUMENT RELATIVE TO A TARGET OBJECT

The present patent document claims the benefit of German Patent Application No. 10 2020 200 239.8, filed Jan. 10, 2020, which is hereby incorporated by reference in its entirety.

TECHNICAL FIELD

The disclosure relates to an apparatus for fixing a target object in place and for orienting an instrument relative to the target object and to a corresponding method.

BACKGROUND

In many industrial and medical applications, precisely orienting or positioning one or more objects, instruments or devices is particularly important for providing success. An example of such applications are medical neurointerventions in which, for example, a medicine is to be administered directly into a specific brain area or, for example, ablation energy is to be applied locally to a specific brain area, for which purpose a corresponding instrument is oriented and guided as precisely as possible to the respective target site. Precise orientation of the respective instrument before the start of the actual intervention, (for example, before penetrating a cranial bone or other brain areas), is of particular significance for the success of the respective treatment and likewise for minimizing the burden on the patient, because any lateral movement or tilting of the respective instrument during the intervention may injure other brain areas.

Prior practice for such applications, (e.g., in the context of a magnetic resonance-guided neurosurgical procedure), has been to mount a guide frame on the patient's skull. The patient is for this purpose shaved over a large area at a suitable fastening point and the guide frame screwed into the patient's cranial bone at a number of locations. For fine adjustment, (e.g., for arranging and orienting the guide frame and thus the instrument to at least millimeter accuracy), a guide rail or the like, along which part of the guide frame is displaceable, may then be provided for each dimension or direction.

This practice is not only a burden on the individual patient but also involves high costs, which may currently be as much as USD 20,000 per application, and is thus in many cases prohibitively costly.

SUMMARY AND DESCRIPTION

The object of the present disclosure is to provide a particularly inexpensive and gentle option for orienting an instrument relative to a target object. The scope of the present disclosure is defined solely by the appended claims and is not affected to any degree by the statements within this summary. The present embodiments may obviate one or more of the drawbacks or limitations in the related art.

An apparatus serves, (e.g., is configured and designed), to fix a target object in place and to orient an instrument relative to the target object which has been fixed in place by the apparatus. The apparatus may be a medical apparatus and the instrument accordingly a medical instrument. The target object may be an object for treatment, a patient or part of a patient, (e.g., a patient's head). The present disclosure is explained for this example or application. It should, however, be emphasized that the present disclosure is not limited to this example or application and is therefore thus likewise usable for other medical or non-medical, (e.g., industrial), applications or purposes.

The apparatus includes an inner first mask element and an outer second mask element which, during intended use of the apparatus, is or has been arranged on an outer side of the first mask element remote from the target object. The two mask elements may be configured and arranged to cover or surround the target object at least in places during intended use of the apparatus. The apparatus further includes at least one retaining or base element to which the first mask element for fixing the target object in place and the second mask element are fastened during intended use of the apparatus. The base element and the two mask elements may have corresponding fastening elements or facilities and be configured for fastening the mask elements to the at least one base element.

Openings for a screw fastening, hooks, or eyes and/or the like may additionally be provided for this purpose. In other words, the at least one base element thus serves for retaining or immobilizing the mask elements which are thus fastened or immobilized or fastenable or immobilizable on the base element(s).

The two mask elements may be fastened to one and the same base element which may have a one-piece construction. Separate base elements or separate parts of the base element may likewise be provided for fastening each of the mask elements.

The at least one base element may take the form of a frame or frame element in order to surround the target element at least in places, (e.g., at two mutually opposing sides), during intended use of the apparatus. The base element may have an at least substantially U-shaped form with a straight or curved bottom and two directly adjoining limbs in order to surround the target object on at least three sides.

In order to fix the target object in place, the first mask element may be or have been tensioned, in particular tightly, over the target object on the base element.

The apparatus further includes an adjusting facility which, during intended use of the apparatus, is mechanically coupled to the second mask element and is designed for mechanically shifting, (e.g., positioning or orienting), the second mask element relative to the first mask element. Such shifting or displacement of the second mask element relative to the first mask element means that the instrument optionally fastened to or mounted on the second mask element may be oriented, (e.g., displaced and/or tilted), relative to the first mask element and thus also relative to the target object optionally fixed in place thereby.

In order to fasten the instrument to the second mask element, the instrument may be inserted into or through the second mask element or a corresponding opening in the second mask element. A guide frame or the like may likewise be fastened, (e.g., adhesively bonded), to the second mask element and the instrument may be held or guided by this guide frame. In the latter case, the instrument may be particularly effectively displaced. In the former case, e.g., if the instrument is also guided or inserted in or through the first mask element, the instrument may be particularly effectively tilted. This is the case because, during intended use of the apparatus, the first mask element remains fixed in place or position during shifting of the second mask element by the adjusting apparatus, e.g., by the actuation thereof. A point or region at which the instrument passes through the first mask element then forms a tilting or swivel point about which the instrument is tilted or swiveled by shifting or displacing the second mask element.

The apparatus is thus here made up of a plurality of individual parts. These individual parts may initially, (for example, on delivery of the apparatus before the intended use thereof on a specific target object), at least in part be separate from one another and only be joined together at the time of or during intended use, e.g., when the apparatus is put into service. The relative position or arrangement of the individual parts of the apparatus relative to one another may in this respect thus depend on an operational or service state of the apparatus. This is taken into account in the present disclosure by the individual parts of the apparatus being described during intended use of the apparatus.

The mask elements may be at least substantially of mat-like or mat-type form, e.g., have a small (material) thickness relative to the main area of extension of the mask elements. As a result, the mask elements may, for the intended use of the apparatus, be laid directly or indirectly from the outside onto the respective target object. Advantageously, a particularly large area of contact at least between the inner first mask element and the respective target object may be achieved. As a result, a correspondingly large adhesion or retention force, (e.g., due to a correspondingly high frictional resistance), may advantageously be effected or applied and thus the target object may be fixed in place particularly effectively and at the same time, thanks to the two-dimensional distribution of the retention force, particularly gently or with little discomfort. The mask elements are here advantageously fastened to, (e.g., screwed into), the base element and not the target object itself. As a result, the burden on or injury to the target object may be significantly reduced in comparison with the initially described conventional technique. It has additionally been found in practice that, in comparison with the above-described conventional technique, the apparatus proposed here generates significantly lower costs which may at present be several orders of magnitude lower.

In one advantageous configuration, the adjusting facility includes at least one eccentric element, e.g., at least one eccentric screw or at least one eccentric joint. During intended use of the apparatus, the second mask element to which at least one base element is fastened and/or a first base element, to which the first mask element is fastened, and a second base element, to which the second mask element is fastened, are joined together by the eccentric element. In both cases, the second mask element may be shifted relative to the first mask element by rotating or actuating the eccentric element.

In the latter configuration, the two mask elements may thus in each case be fastened to their own frame or base element and these two frame or base elements may then be shifted relative to one another. This has the advantage that, irrespective of how they are shifted or adjusted, the mask elements may in each case always be and remain fastened with the optimum tension to the respective base element.

The first configuration, on the other hand, may have the advantage of a more compact structure. The tension of the second mask element may here be maintained at least substantially unchanged when it is shifted if a plurality of eccentric elements are provided on different sides and a plurality of these eccentric elements are actuated when the second mask element is shifted. If, during intended use of the apparatus, the second mask element is arranged on the at least one base element by the eccentric element, the eccentric element may thus advantageously be configured multifunctionally both for fastening or retaining the second mask element and for displacing it. As a result, the complexity and thus the effort and costs involved in the production and operation of the apparatus may be reduced or kept particularly low.

On rotation or actuation of the eccentric element, the second mask element or the base element thereof may be shifted relative to an axis of rotation of the eccentric element by an eccentric part of the eccentric element. The second mask element may to this end be fastened to the eccentric part of the eccentric element or be mechanically connected to the eccentric part.

The arrangement described here advantageously enables relatively accurate, reliably reproducible, manually and/or automatically performable displacement of the second mask element and in addition is advantageously particularly simply and inexpensively achievable.

The adjusting facility may include a plurality of eccentric elements which may be arranged in a spatially distributed manner, e.g., along an outer region or periphery of the second mask element and/or along the at least one base element. Particularly flexible and accurate displacement of the second mask element and thus particularly flexible and accurate orientation of the instrument may advantageously be achieved as a result.

In a further advantageous configuration, the mask elements each have, in a respective central region spaced from the at least one base element, a plurality of openings passing through the respective mask element. In other words, the mask elements are thus perforated with a plurality of holes or apertures in a spatially distributed arrangement. The openings may be arranged randomly or in a predetermined, regular pattern. Thanks to the openings, it is advantageously possible to design the mask elements in an air-impermeable manner, while advantageously also permitting the circulation of air for ventilation of the particular target object during intended use of the apparatus. If the target object is a patient, their comfort during use of the apparatus may be significantly increased.

The openings may advantageously optionally serve for passage of and/or fastening the instrument or an instrument mount or instrument guide. This advantageously enables particularly simple use of the apparatus. The openings may likewise serve or be used as fastening orifices for fastening the mask elements to the at least one base element. Because a plurality of openings in a spatially distributed arrangement are provided, these functions may advantageously be particularly flexibly embodied or used, e.g., for target objects of differing sizes or shapes, in a particularly simply and reliable manner. Accordingly, depending on requirements, for example, depending on the size and/or shape of the target object, different ones of the openings may be used for passage or fastening of the instrument or instrument mount or guide to the second mask element or to both mask elements and/or for fastening the mask elements to the at least one base element.

The mask elements may be, in each case, individually shaped to the respective target object or be shaped during intended use of the apparatus. A further advantageous configuration provides to this end that the two mask elements are fabricated from a thermoplastic material. In other words, the mask elements are thus elastically or plastically deformable when they are heated at least up to their glass transition temperature or softening temperature. Below these temperatures, however, the material of the mask elements is solid, such that they retain the shape or form imparted or fashioned in the heated state. The mask elements may be fabricated from a material which has a glass transition temperature or a softening temperature of at most 50° C. It may thus advantageously be possible to heat at least the inner first mask element up to its glass transition temperature or softening temperature and then to adapt it directly on the respective target object, (e.g., a patient), to the outer shape or form thereof, e.g., to shape it thereto, and then to allow it to solidify, e.g., become solid. The second mask element may then optionally be applied in corresponding manner while the target object is fixed in place by the first mask element.

All in all, a particularly accurately fitting shape of the mask elements which is individually configured to, (e.g., shaped to), the respective target object may be enabled or achieved in this way. This advantageously in turn allows the target object to be fixed in place particularly stably and reliably by the first mask element while at the same time advantageously in each case a particularly low or two-dimensionally particularly uniform load is applied to the target object. Thanks to the shape of the second mask element being at least substantially similar to that of the first mask element, it is advantageously additionally possible to achieve or enable particularly precise relative displacement or orientation of the second mask element relative to the first mask element. Thanks to the individual shaping or shape-ability of the mask elements to the respective target object, it is additionally possible to achieve particularly accurate and reliable reproducibility in the event of repeated use of the apparatus, in which the mask elements already shaped to the respective target object are repeatedly used for the same target object at different points in time. In addition, the ability to reuse the mask elements once they have been shaped and then solidified for the respective target object further reduces the burden on the target object, (e.g., due to a reduction in the time required and reduced exposure to high temperatures in the event of repeated use of the apparatus). In the configuration proposed here, the mask elements may optionally additionally be reusable for different target objects, so enabling further materials and costs savings for the apparatus or the use thereof.

In one advantageous development, the two mask elements are formed or fabricated from different thermoplastic materials, wherein the glass transition temperature or softening temperature of the inner first mask element is higher than that of the outer second mask element. In other words, the materials of the mask elements are thus configured or selected such that, at the glass transition temperature or softening temperature of the material of the second mask element, the second mask element is elastically or plastically deformable, while the first mask element is solid, e.g., neither plastically nor elastically deformable. As a result, when the apparatus is used, the first mask element may firstly be accurately shaped to fit the respective target object and then fix the latter reliably, stably, and enduringly in place, while the second mask element may be or have been shaped to the target object or to the first mask element. The material of the second mask element may be in a plastically or elastically deformable state without its temperature significantly softening the material of the first mask element. This advantageously enables particularly simple use of the apparatus.

The actual glass transition temperatures or softening temperatures and thus the materials to be used may be or have been selected as a function of the respective intended application, for example of the thermal sensitivity of the respective intended target object, and/or as a function of the respective ambient conditions during use of the apparatus. Depending on requirements, it is thus possible to select known thermoplastic materials which are currently readily commercially available, (e.g., a polyolefin, ABS, PA, PLA, PMMA, PC, PET, PEEK, PVC, celluloid, and/or the like or a mixture of a plurality of these or other materials).

In a further advantageous configuration, at least one reinforcing element, (e.g., an aramid structure), is integrated into each of the mask elements. The mask elements or the materials thereof may be aramid-reinforced, for example, by integrating or incorporating aramid fibers or an aramid braid or aramid mat in a carrier or envelope material of the mask elements. Such a reinforcing element or such integrated reinforcement may advantageously increase, (e.g., improve), the dimensional stability of the mask elements. As a result, it is turn advantageously possible to achieve particularly stable and reliable fixing in place of the target object and/or particularly accurate, reliable, and particularly readily reproducible shiftability or relative positioning of the second mask element, (e.g., relative to the first mask element, the target object, and/or the at least one base element).

The reinforcing element may additionally predetermine a basic shape or rough shape of the mask elements. As a result, in particular in the case of a thermoplastic configuration of the mask elements, costs for shaping the mask elements to the respective target object may optionally be reduced. Shaping of the mask elements to the respective target object may likewise optionally be facilitated, because the reinforcing element is capable of reducing the risk of the mask elements completely losing their shape, (e.g., completely melting or liquefying). The reinforcement may likewise increase the tensile strength of the mask elements, (e.g., of the first mask element), whereby a higher tension and thus improved fixing in place of the target object may advantageously be achieved.

A further aspect is a method for orienting an instrument (e.g., medical instrument) relative to a respective predetermined target object. The method may be performed by the apparatus. The method may accordingly also serve, (e.g., be performed), for fixing the respective target object in place by the apparatus.

In one method act of the method, the inner first mask element is applied to the respective target object and then immobilized on the at least one base element in order to fix the target object in place. Before or during this act, the first mask element, (e.g., in the case of a thermoplastic configuration), may firstly be heated, (for example, up to its glass transition temperature or softening temperature), and shaped on the respective target object, e.g., configured to the shape thereof. In this case, after being shaped and before being immobilized on the at least one base element, the first mask element may then be cooled to below its glass transition temperature. The first mask element may, however, likewise also be immobilized or screwed to the base element, (e.g., the first mask element is cooling), whereby particularly gentle fixing in place of the target object may optionally be enabled.

In a further method act of the method, the outer second mask element is applied to the outside of the first mask element and likewise at least in places surrounding or covering the respective target object and is fastened to or immobilized on the at least one base element.

In a further method act of the method, the second mask element is then shifted relative to the first mask element, and thus also relative to the target object which has been fixed in place, by the adjusting facility mechanically coupled to the second mask element. As a result, an instrument optionally fastened to or passed through at least the second mask element may be oriented relative to the target object.

Application of the mask elements may in each case mean or involve, for example, laying on a mat-like or mat-type material of the respective mask element, pouring over the respective liquefied or softened material of the respective mask element, and/or the like.

The method may thus be a method for using or operating the apparatus. Accordingly, some or all of the operations, procedures, or measures described in connection with the apparatus may be provided as optional further method acts of the method. The apparatus may likewise be configured and designed for performing or using the method. The apparatus may to this end have properties, features, and/or components optionally described in connection with the method.

In a further advantageous configuration, a tubular, (e.g., hollow-cylindrical), guide sleeve is arranged in a passage orifice or opening which passes through one of the two mask elements at a predetermined position. This passage orifice may here already be present or be formed during production of the mask elements. The passage orifice may likewise be produced once the mask elements have been shaped to the respective target object, (e.g., by drilling through or piercing the two mask elements). The tubular guide sleeve may then advantageously reinforce and/or stabilize the passage orifice. Thanks to the guide sleeve, it is thus advantageously possible to create or provide a defined, reinforced passage or aperture through the two mask elements.

The guide sleeve, with or without a further instrument arranged or guided therein or thereon, may be oriented by the adjusting facility by shifting the second mask element. In the former case, the instrument may thus be indirectly positioned and oriented by orienting the guide sleeve, while in the latter case the guide sleeve may itself be the instrument for the purposes of the present disclosure.

In either case, the tubular guide sleeve provided here may advantageously improve the accuracy, reliability, and reproducibility of the orientation or movement of the further instrument, in particular, if the tubular guide sleeve extends outwards in the direction away from the target object through the outer second mask element. Thanks to the guide sleeve, a further instrument, (e.g., a needle, a drill, an ablation instrument, and/or the like), may be guided to the target object with reduced lateral movement latitude in comparison with orientation and guidance solely by the two mask elements. Providing the mask elements are formed from a thermoplastic material, the guide sleeve may advantageously be introduced into or pushed or passed through the mask elements in the heated, (e.g., softened or deformable), state of the elements. On cooling and solidification of the material of the mask elements, the material may then connect to the introduced guide sleeve and so particularly simply and reliably hold or fix it in place.

In a further advantageous configuration, a spacer element or spacer, (e.g., fabricated from a thermally insulating material), is applied to the first mask element prior to application of the second mask element and the second mask element is then applied to the outside of the spacer element. In other words, the second mask element is thus applied onto an outer side of the spacer element remote from the first mask element and is thus spaced from the first mask element by the spacer element. The spacer element may have a (material) thickness of one or more millimeters. The spacer element advantageously makes it possible to form the second mask element in a shape which is particularly consistently and uniformly enlarged relative to the first mask element and in line with the thickness of the spacer element, wherein the second mask element may however still advantageously follow the shape or contour of the first mask element, which shape or contour is in this case advantageously modeled or reproduced by the spacer element.

The spacer element may be fabricated from a flexible or elastic material, for example, from a foam or the like. As a result, it is particularly straightforwardly capable of reproducing the shape of the first mask element. The spacer element may be laid onto or adhesively bonded to the first mask element. The latter may be advantageous if, for the remainder of the method, (e.g., during further use or application of the apparatus), the spacer element remains or is left in place between the two mask elements. The former, on the other hand, may be particularly advantageous if the spacer element is removed or taken away, (e.g., after shaping and solidification of the second mask element), such that it is then no longer located between the two mask elements for the remainder of the method, (e.g., during further use or application of the apparatus). Removing or taking away the spacer element in this manner may advantageously be facilitated by applying an antistick agent, (e.g., a PTFE spray), to the spacer element and/or to the sides of the first and/or second mask element facing the spacer element.

Thanks to the spacer element, it is advantageously possible to reduce exposure of the target object and/or the first mask element to heat on application of the second mask element, in particular, if the spacer element is fabricated from a thermally insulating material. This may be particularly advantageous if the second mask element is formed from a thermoplastic material because the material of the second mask element may then without any disadvantage be heated to a higher temperature for shaping. This may bring about a lower viscosity and thus better flowability and moldability or shape reproduction capability of the material of the second mask element and may thus ultimately lead to more accurate or more detailed shaping of the second mask element. Greater flexibility in material selection for the second mask element may likewise consequently be offered or achieved.

If the spacer element is left in place between the two mask elements during the method, in particular, during shifting of the second mask element, more readily predictable or reproducible, particularly consistent and uniform movement or shiftability of the second mask element may be obtained as a result. If, on the other hand, the spacer element is removed or taken away after application or shaping of the second mask element, it is advantageously possible as a result to improve, for example, ventilation and thus comfort for the respective target object. In either case, a further advantage of the spacer element may be that it is possible, when applying the second mask element, to prevent it from becoming materially bonded to the first mask element. As a result, it may particularly reliably be provided that the second mask element remains separately and independently movable from the first mask element, so simplifying the application and performance of the method.

In a further advantageous configuration, a suitable or necessary setting for the adjusting facility in order to achieve a predetermined target orientation of the instrument is automatically determined and output by a data processing facility on the basis of a predetermined model of the apparatus. The predetermined target orientation of the instrument may be predetermined as a vector or direction, by coordinates of a target region or region of interest (RoI) of the target object which is to be reached by the instrument, by coordinates of an application or contact point at which the instrument is to be brought into contact with the target object and/or the like.

The target orientation or corresponding orientation data may be acquired or received by the data processing facility via a corresponding interface and automatically supplied to the model as input data or parameter values. The model may then simulate the apparatus and its behavior, (e.g., by modeled, simulated, or virtual actuation or adjustment of the adjusting facility). The model or a corresponding computer program or corresponding program code may be executed by the data processing facility. The data processing facility may have a processor. The data processing facility may likewise have a data memory connected to the processor, wherein the model or a corresponding computer program or corresponding program code of the model or for execution of the model may be stored. The data processing facility may thus here take the form of a computer. Thanks to the automatic computer- or model-based computation of the respectively suitable or necessary setting of the adjusting facility, it is advantageously possible to achieve a particularly accurate and reliable orientation of the instrument.

In addition, details, descriptions, or properties of the respective target object and/or of the two mask elements and/or of a respective current actual state of the adjusting facility and/or the like may also be provided or supplied to the data processing facility or the model as further input data or parameter values and thus received by the data processing facility or the model. Corresponding input data may be predetermined and/or have been entirely or in part acquired, (e.g., automatically), by sensors. For example, a medical image data set, (e.g., a CT or MR image data set), of the target object may be provided or acquired in order to describe or characterize the target object. The apparatus, (e.g., including the target object fixed in place therewith or therein), may likewise be acquired, (e.g., optically), such as by a camera or the like. Thanks to the corresponding image or camera data, it is possible to acquire, (e.g., state or characterize), not only the target object but likewise, insofar they are imaged, the mask elements and/or an actual state of the adjusting facility. Such image or camera data may then be supplied directly to the model or first be processed or evaluated, (e.g., by the or a further data processing facility), in order to determine specified variables or parameter values of the imaged object. A predetermined image processing and/or object recognition algorithm may be used for this purpose.

The data processing facility may here be part of the apparatus or separate therefrom. The suitable or necessary setting of the adjusting facility determined by the data processing facility may be output as a message or indication for a respective user or as a control signal for an automatic or partially automatic actuation or control facility of the adjusting facility for automatically carrying out or moving to the specific setting. In the latter case, the instrument may advantageously be particularly accurately, reproducibly, and reliably oriented.

It should be noted at this point that the present disclosure, in particular the present method, includes and claims the described acts or sequences only of exclusively stated or indicated surgical acts or measures. Actual use of the instrument for treatment of the target object, for example, is accordingly not part of the method.

The properties and further developments of the apparatus and of the method stated previously and below and the corresponding advantages are in each case mutatis mutandis reciprocally transferable between these aspects of the disclosure. The disclosure thus also encompasses those further developments of the imaging apparatus and of the method which include refinements which, in order to avoid unnecessary redundancy, are not here explicitly separately described in the respective combination or for each of these aspects of the present disclosure.

BRIEF DESCRIPTION OF THE DRAWINGS

Further features, details, and advantages of the present disclosure are revealed by the following description of exemplary embodiments and with the assistance of the drawings, in which.

DETAILED DESCRIPTION

In the exemplary embodiments, the described components of the embodiments are in each case individual features of the disclosure to be considered independently of one another, which in each case also mutually independently further develop the disclosure and are therefore to be considered part of the disclosure either individually or in a combination other than that indicated. The described embodiments may furthermore also be supplemented by further, previously described features of the disclosure.

For clarity's sake, identical, functionally identical, or mutually corresponding elements are in each case designated in the figures with the same reference signs, even if different instances or examples of the corresponding elements may be involved.

Figure 1:
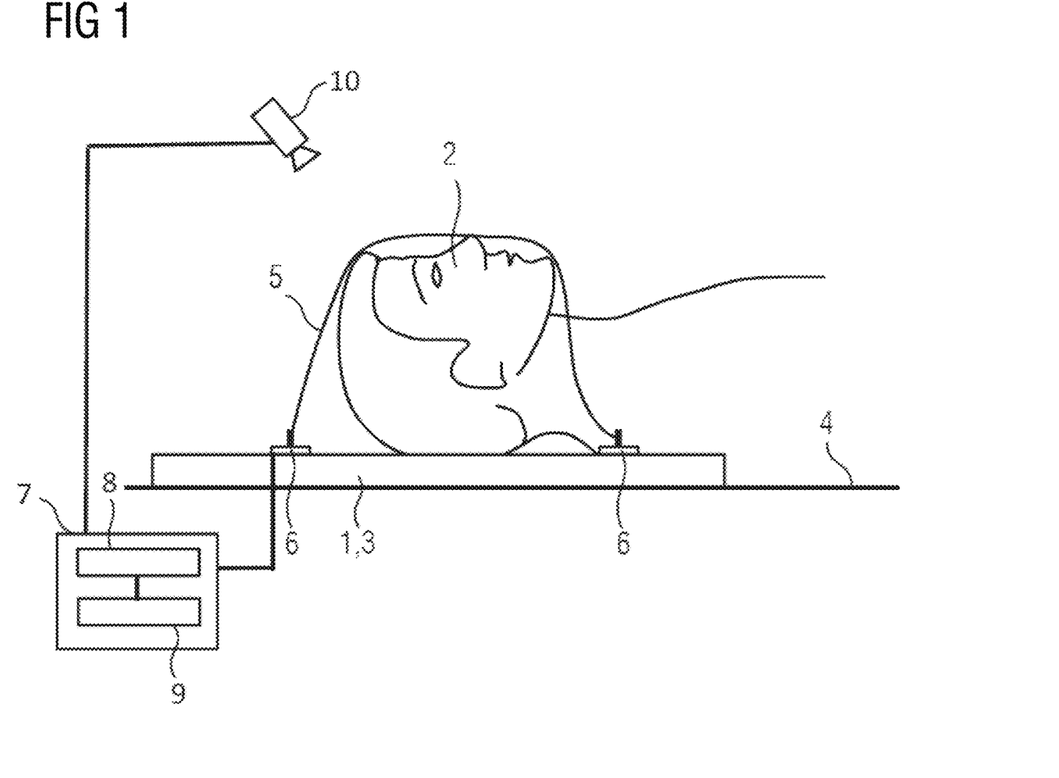
FIG. 1 depicts a schematic partial perspective view of an example of an apparatus for fixing a patient in place and for orienting an instrument (not shown).

FIG. 1 depicts a schematic partial perspective representation of an apparatus 1 for fixing a target object in place and for orienting an instrument 15 (see FIG. 2) relative to the target object. The target object is in the present case a here likewise schematic partial representation of the patient 2, in particular of the patient's head. The apparatus 1 here has a base or frame element 3 which, in the present case, is at least substantially U-shaped and surrounds the target object, here the head of the patient 2, on at least three sides. The frame element 3 is here connected to a patient table 4 on which the patient 2 is in the present case lying.

In order to fix the head of the patient 2 in place, e.g., to hold or position it stationarily, a first mask element 5 is tensioned at least in places over the patient 2 and immobilized on the frame element 3 by a plurality of fastening elements 6.

A data processing facility 7 with a processor 8 and a data memory 9 connected thereto and an acquisition facility 10 are additionally shown here schematically. The acquisition facility 10 is in the present case capable of acquiring the apparatus 1 and the head of the patient 2 fixed in place therein and transmitting corresponding acquisition data to the data processing facility 7. The data processing facility 7 and/or the acquisition facility 10 may here be part of the apparatus 1 or merely connected thereto.

Figure 2:
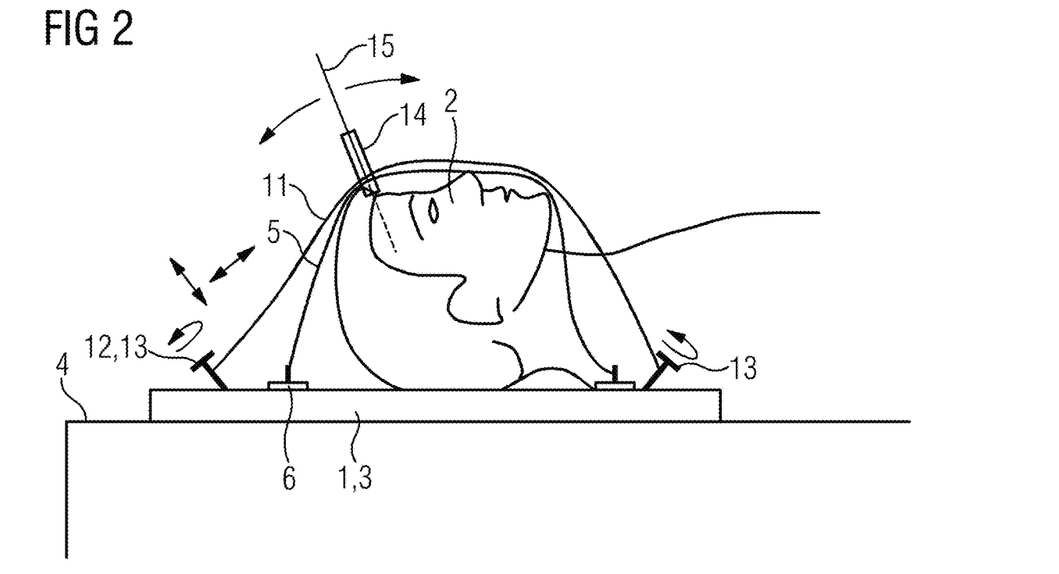
FIG. 2 depicts a further schematic representation to illustrate an example of the apparatus.

FIG. 2 depicts a further partial schematic representation of the apparatus 1 or of a corresponding apparatus 1. In this case too, the patient 2 is fixed in place by the first mask element 5 in or to the apparatus 1. In addition, a second mask element 11 is here tensioned over the head of the patient 2 on the outside of the first mask element 5. The second mask element 11 is here likewise fastened to the frame element 3 by an adjusting facility 12. Although the fastening element 6 and the adjusting facility 12 are here each shown as independent parts, they may likewise be combined or integrated into a single element or component. In other words, the first mask element 5 and the second mask element 11 may thus optionally together be fastened to the frame element 3 by the adjusting facility 12. Each of the mask elements 5, 11 may likewise be provided with its own frame element 3. These respective frame elements 3 may then be or have been fastened to one another and/or in each case to the patient table 4. Thanks to the adjusting facility 12, the frame element 3 of the second mask element 11 may then be shifted relative to the frame element 3 of the first mask element 5. The frame element 3 of the second mask element 11 may thus here be connected via the adjusting facility 12 to the patient table 4 and/or to the frame element 3 of the first mask element 5. Here too, actuation of the adjusting facility 12 then enables a corresponding defined shift or displacement of the two mask elements 5, 11 relative to one another.

The adjusting facility 12 here includes at least one screw 13, (e.g., a plurality of eccentric screws). By rotation of the eccentric screws 13, the second mask element 11 retained thereby or the frame element 3 thereof, to which the second mask element 11 is fastened, may be shifted relative to the first mask element 5 or relative to the frame element 3 thereof or the part of the frame element thereof to which the first mask element 5 is fastened, and thus also relative to the patient 2 who has been fixed in place.

The two mask elements 5, 11 are here pierced by a guide sleeve 14 at a predetermined position. The instrument 15 may in the present case be guided through the guide sleeve 14 and brought into contact with the patient 2. On actuation of the adjusting facility 12 or of the eccentric screws 13, not only the second mask element 11, but also the guide sleeve 14 and optionally the instrument 15 guided therein are thus shifted, in particular tilted and thus oriented relative to the patient 2.

Figure 3:
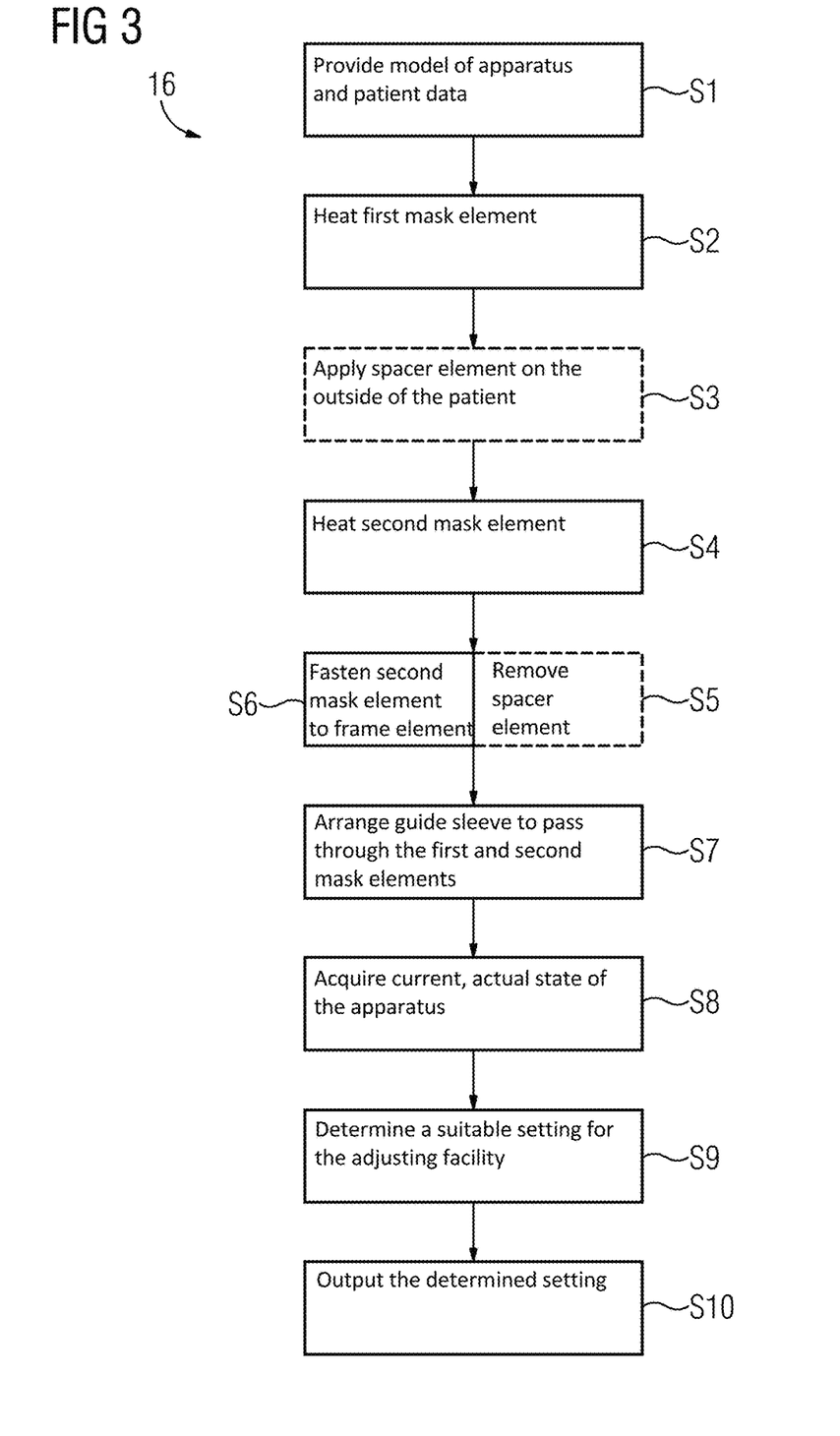
FIG. 3 depicts an exemplary schematic sequence chart for a method for fixing the patient in place and for orienting the instrument.

Use or a method for the use of the apparatus 1 will be explained below with the assistance of an exemplary sequence chart 16 shown schematically in FIG. 3 with reference to FIG. 1 or FIG. 2.

A model of the apparatus 1 and patient data of the patient 2 are provided in method act S1. The data may include a 3D model or a 3D image data set of the patient 2, a target region or region of interest for the instrument 15 and/or a predetermined target orientation of the instrument 15.

With the patient 2 arranged in the apparatus 1, the thermoplastic first mask element 5 is heated in method act S2 such that it is elastically or plastically deformable. In this state, the first mask element 5 is then shaped on the patient 2. Before, during or after cooling, and thus solidification, of the first mask element 5, the latter is then fastened, as shown in FIG. 1, to the frame element 3. As a result, the patient 2 is fixed in place relative to the apparatus 1. Because the apparatus 1 may in turn be immobilized on the patient table 4 or integrally constructed therewith, it is possible to set and maintain a predetermined pose of the patient 2.

In optional method act S3, an in particular thermally insulating spacer element may be applied on the outside, e.g., on the side remote from the patient 2, of the first mask element 5.

In method act S4, the thermoplastic second mask element 11 is heated such that it is elastically or plastically deformable. In this state, the second mask element 11 is applied onto the outside of the first mask element 5 or the spacer element and shaped.

Once the second mask element 11 has cooled and solidified, the optionally applied spacer element may be removed in optional method act S5.

The second mask element 11 is fastened to the frame element 3 in method act S6. This may proceed before, during or after complete hardening of the second mask element 11 and/or removal of the spacer element. Depending, for example, on the application and/or material selection or temperature of the second mask element 11, different variants, combinations or sequences of the described procedures may here be used to achieve an optimum result.

It may likewise be possible to remove the solidified first mask element 5 and/or the spacer element shaped thereon, and thus detach it from the patient 2, and then to shape the second mask element 11 thereon. In other words, the second mask element 11 may in this respect thus be shaped "offline" while nevertheless reproducing the shape of the patient 2, because the shape is then provided by the first mask element 5 already correspondingly shaped to the patient 2 or the correspondingly shaped spacer element. Thanks to the second mask element 11 being separately shaped, (e.g., remotely from the patient 2), the burden on the patient may possibly be reduced, a higher temperature may be used for the second mask element 11, or a material may be used for the second mask element 11 which would otherwise not be practical.

In method act S7, (e.g., with the mask elements 5, 11 fastened to the frame element 3), the guide sleeve 14 is arranged to pass through the two mask elements 5, 11. To this end, for example, using a drill compatible with the respective application, (e.g., by an MR-compatible drill), a hole may be drilled at a predetermined position through both masks 5, 11 and the guide sleeve 14 inserted or placed in this hole or bore. Additionally or alternatively, the mask elements 5, 11 may be locally heated at the predetermined position and then pierced by the guide sleeve 14. Ultimately, however, use of the guide sleeve 14 may be optional.

In method act S8, which is likewise possibly optional, a current actual state of the apparatus 1 of the patient 2 is acquired by the acquisition facility 10 as indicated in FIG. 1 and transmitted to the data processing facility 7. This actual state, which may indicate a spatial position of the patient 2 who has been fixed in place and a current setting of the adjusting facility 12, may be acquired while the patient 2 is fixed in place by the first mask element 5 and the latter is overlaid by the second mask element 11.

In method act S9, based on the actual state and the predetermined model of the apparatus 1, the data processing facility 7 determines a suitable setting for the adjusting facility 12, which setting enables or achieves a predetermined or desired orientation of the instrument 15 or the guide sleeve 14. In the present case, corresponding software or a computer program may automatically determine a necessary or suitable setting or rotation of the eccentric screw 13, (or, for example, an alternatively used eccentric joint or the like), for setting or achieving the predetermined target orientation of the instrument 15, (e.g., a specific angle according to a predetermined planned entry path for the instrument 15).

In method act S10, the setting determined in this manner for the adjusting facility 12 is output and/or automatically or semi-automatically executed or set. Depending on the configuration of the apparatus 1 or of the adjusting facility 12, this may be carried out automatically or a respective user may be assisted in setting or executing the specific setting, for instance, by appropriate acoustic and/or optical and/or tactile instruction signals. A setting direction, a setting scope and/or the achievement of the specific setting may for instance be stated or indicated in this manner.

The described examples show overall how a mask may be fixed in place and an instrument 15, for example for an intervention needle, may be oriented inexpensively and in a manner, which is particularly gentle on the patient 2.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described in detail with reference to the exemplary embodiments, it is not limited by the disclosed examples and a person skilled in the art may derive other variations herefrom without departing from the scope the disclosure.

The invention claimed is:

1. An apparatus for fixing a target object in place and for orienting an instrument relative to the target object which has been fixed in place, the apparatus comprising:
    at least one base element;
    a first mask element comprising a first thermoplastic material having an opening in the first mask element, wherein the first mask element is configured to at least partially cover the target object and fix the target object in place between the first mask element and the at least one base element, wherein the first mask element is fastened to the at least one base element, and wherein the first mask element is configured to be shaped to a surface of the target object;
    a second mask element comprising a second thermoplastic material having an opening in the second mask element, wherein the second mask element is configured to at least partially cover the target object, wherein the second mask element is fastened to the at least one base element, and wherein the second mask element is shaped on top of an outer surface of the first mask element such that the first mask element is positioned between the target object and the second mask element;
    a guide sleeve configured to receive the instrument, wherein the guide sleeve extends through both the opening in the first mask element and the opening in the second mask element; and
    an adjusting facility mechanically coupled to the second mask element,
    wherein the adjusting facility is configured to mechanically shift the second mask element relative to the first mask element, and
    wherein the guide sleeve is configured to be shifted and reoriented relative to the target object by the mechanically shifting of the second mask element relative to the first mask element via the adjusting facility.

2. The apparatus of claim 1, wherein the instrument is a medical instrument.

3. The apparatus of claim 1, wherein the at least one base element comprises a first base element and a second base element, wherein the first mask element is fastened to the first base element, wherein the second mask element is fastened to the second base element, and wherein the first base element and the second base element are joined together.

4. The apparatus of claim 1, wherein the adjusting facility comprises at least one eccentric element, and
    wherein the second mask element is configured to be shifted by rotating the at least one eccentric element.

5. The apparatus of claim 1, wherein the first mask element and the second mask element each has, in a respective central region spaced from the at least one base element, a plurality of openings passing through the first mask element or the second mask element respectively.

6. The apparatus of claim 1, wherein the first thermoplastic material of the first mask element and the second thermoplastic material of the second mask element each has a glass transition temperature or softening temperature of at most 50° C.

7. The apparatus of claim 1, wherein the first thermoplastic material of the first mask element and the second thermoplastic material of the second mask element are different thermoplastic materials, and
    wherein a glass transition temperature or softening temperature of the first thermoplastic material of the first mask element is higher than a glass transition temperature or softening temperature of the second thermoplastic material of the second mask element.

8. The apparatus of claim 1, further comprising:
    at least one reinforcing element,
    wherein the at least one reinforcing element is integrated into at least one mask element of the first and second mask elements.

9. The apparatus of claim 8, wherein the at least one reinforcing element is an aramid structure.

10. The apparatus of claim 1, further comprising:
    the guide sleeve configured to pass through the opening of the first mask element and the opening of the second mask element,
    wherein the guide sleeve is configured to receive the instrument.

11. The apparatus of claim 1, wherein the adjusting facility is fastened to the at least one base element.

12. The apparatus of claim 1, wherein a point or a region at which the guide sleeve passes through the opening in the first mask element provides a swivel point about which the guide sleeve is swiveled by the mechanically shifting of the second mask element.

13. A method for orienting an instrument relative to a target object, the method comprising:
    providing at least one base element;
    applying a first mask element of an apparatus to the target object; the first mask element comprising a first thermoplastic material having an opening in the first mask element;
    immobilizing the first mask element on the at least one base element of the apparatus to fix the target object in place; wherein the first mask element is configured to at least partially cover the target object and fix the target object in place between the first mask element and the at least one base element, wherein the first mask element is fastened to the at least one base element, and wherein the first mask element is configured to be shaped to a surface of the target object;
    applying a second mask element of the apparatus on top of an outer surface of the first mask element, wherein the second mask element comprises a second thermoplastic material having an opening in the second mask element, wherein the second mask element is configured to at least partially cover the target object, wherein the second mask element is fastened to the at least one base element; and wherein the second mask element is shaped on top of the outer surface of the first mask element such that the first mask element is positioned between the target object and the second mask element;

providing a guide sleeve through both the opening in the first mask element and the opening in the second mask element, wherein the guide sleeve is configured to receive the instrument;

and mechanically shifting the second mask element relative to the first mask element by an adjusting facility of the apparatus that is mechanically coupled to the second mask element; wherein the guide sleeve is shifted and reoriented relative to the target object by the mechanically shifting of the second mask element relative to the first mask element via the adjusting facility.

14. The method of claim 13, wherein the instrument is a medical instrument.

15. The method of claim 13, further comprising: automatically determining a setting for the adjusting facility in order to achieve a predetermined target orientation of the instrument based on a predetermined model of the apparatus; and outputting, by a data processing facility, the setting.

* * * * *